United States Patent
Dabelstein et al.

(10) Patent No.: US 9,753,072 B2
(45) Date of Patent: Sep. 5, 2017

(54) MAGNETIC COUPLING FOR ELECTRICAL CONDUCTIVITY ASSESSMENT

(71) Applicant: The Boeing Company, Huntington Beach, CA (US)

(72) Inventors: Donald K. Dabelstein, Renton, WA (US); Andrew M. Robb, Ravensdale, WA (US); Arlene M. Brown, Normandy Park, WA (US)

(73) Assignee: The Boeing Company, Chicago, IL (US)

(*) Notice: Subject to any disclaimer, the term of this patent is extended or adjusted under 35 U.S.C. 154(b) by 353 days.

(21) Appl. No.: 14/459,380

(22) Filed: Aug. 14, 2014

(65) Prior Publication Data

US 2016/0047768 A1  Feb. 18, 2016

(51) Int. Cl.
| | |
|---|---|
| *H04B 5/00* | (2006.01) |
| *G01R 33/54* | (2006.01) |
| *G01R 29/08* | (2006.01) |
| *G01N 27/02* | (2006.01) |

(52) U.S. Cl.
CPC ....... *G01R 29/0835* (2013.01); *G01N 27/025* (2013.01)

(58) Field of Classification Search
CPC ............ G01R 33/3685; G01R 33/3415; G01R 33/3621; G01R 29/0835; H02J 7/025; H04B 5/0037; H04B 5/0093; G01V 3/28
USPC ....... 324/322, 318, 239, 309, 333, 335, 338, 324/339, 343, 347; 455/41.1
See application file for complete search history.

(56) References Cited

U.S. PATENT DOCUMENTS

| | | | | |
|---|---|---|---|---|
| 4,006,405 A | * | 2/1977 | Greenwood | G01B 7/06 324/227 |
| 4,639,669 A | * | 1/1987 | Howard | G01N 9/24 324/229 |
| 6,949,925 B2 | * | 9/2005 | Johnson | G01B 7/10 324/207.26 |

FOREIGN PATENT DOCUMENTS

GB    1007822    10/1965

OTHER PUBLICATIONS

Novel electromagnetic modeling approach of carbon fiber-reinforced polymer laminate for calculation of eddy currents and eddy current testing signals, Journal of Composite Materials 0021998314521475, first published on Feb. 6, 2014.*
Cheng et al., "Novel electromagnetic modeling approach of carbon fiber-reinforced polymer laminate for calculation of eddy currents and eddy current testing signals", Journal of Composite Materials, vol. 49. No. 5, 2014.
Mook et al., "Hochauflosende Verfahren Zur Zerstorungsfreien Prufung", Journal of Mechanical Engineering of the National Technical University of Ukrain, vol. 1, pp. 11-17, 2011.

(Continued)

*Primary Examiner* — Alesa Allgood
(74) *Attorney, Agent, or Firm* — Womble Carlyle Sandridge & Rice LLP

(57) ABSTRACT

A method is provided that includes setting up a composite material structure under test (SUT) between a transmit coil and a receive coil. The transmit coil is driven with a RF signal over a plurality of frequencies, thereby causing the transmit coil to produce a magnetic field that by magnetic coupling through the SUT induces a voltage in the receive coil. The voltage in the receive coil is measured, and from the voltage, a measurement of attenuation of the RF signal caused by the SUT between the transmit coil and receive coil is produced. And an effective conductivity of the SUT is calculated from the measurement of attenuation.

16 Claims, 7 Drawing Sheets

(56) References Cited

OTHER PUBLICATIONS

Schulze et al., "Eddy Current Testing of Carbon Fiber Materials by High Resolution Directional Sensors", vol. 16, No. 5, pp. 791-797, 2010.
Yolken et al., "Nondestructive Evaluation of Advanced Fiber Reinforced Polymer Matrix Composites", A Technology Assessment, 2009.
Li et al., "Characterization of Carbon Fibre Reinforced Composite by Means o Non-Destructive Eddy Current Testing and FEM Modeling", 17th World Conference on Nondestructive Testing, 2008.
European Search Report dated Jan. 18, 2016 for Application No. 15178770.2.
Bowler et al., "Electrical Conductivity Measurement of Metal Plates Using Broadband Eddy-Current and Four-Point Methods," Measurement Science and Technology, vol. 16 (2005), pp. 2193-2200.
Crowley et al., "Contactless Method of Measuring Resistivity," Review of Scientific Instruments, vol. 47, No. 6, Jun. 1976, pp. 712-715.
Lin et al., "Plane-Wave Shielding Characteristics of Anisotropic Laminated Composites," IEEE Transactions on Electromagnetic Compatibility, vol. 35, No. 1, Feb. 1993, pp. 21-27.
Lin et al., "Transient Propagation in Anisotropic Laminated Composites," IEEE Transactions on Electromagnetic Compatibility, vol. 35, No. 3, Aug. 1993, pp. 357-365.
Wiese, "DC Anisotropic Resistivity Sensitivity and Inversion," Ph.D. Thesis, Mar. 2012, The University of Adelaide, School of Chemistry and Physics, Australia, 107 pages.

\* cited by examiner

MAGNETIC COUPLING FOR ELECTRICAL CONDUCTIVITY ASSESSMENT

TECHNOLOGICAL FIELD

The present disclosure relates generally to non-destructive testing (NDT) and, in particular, to NDT of a panel or part with composite material that has electrically conductive properties such as a carbon fiber reinforced plastic (CFRP), boron fiber composite, dielectric composite modified with conductive ingredients, or hybrids with at least one electrically conductive layer.

BACKGROUND

Conventional aluminum aircraft structures typically have inherent lightning protection. An aluminum skin structure has uniform and predictable material properties, including the electrical properties. The electrical conductivity impacts electromagnetic effects (EME) such as lightning, shielding, precipitation static and electrostatic performance. The high conductivity of aluminum provides inherent shielding. Thus currents are conducted on the outside structure, not on internal structures and systems reducing the need for additional protection features such as cable shields or fuel tank sealant to contain sparking Protection against skin puncture by lightning can be provided simply by sizing the aluminum skin thickness. In areas of conventional aircraft structure where the skin is electrically non-conductive, such as radomes and aerodynamic fairings, metal bus bars can be applied to the exterior surface to direct the lightning currents to the aluminum structure. Expanded metal foils, woven wire meshes and interwoven wire forms of lightning protection are often co-cured into a composite as a protective layer to prevent lightning from puncturing the part and/or to provide electromagnetic shielding.

Providing lightning protection for electrically conductive composite material structure, such as carbon fiber reinforced plastic (CFRP), is much more difficult and complicated than for typical aluminum structure. Conductive composites are nonhomogeneous and are considerably less conductive than aluminum. The conductivity of conductive composite material structures such as CFRP panels may therefore be an important parameter to determine the performance of the composite during lightning strike. In another context, the conductivity may be an important parameter to know in the induction heating process involving these structures. Conductivity and thickness also determine shielding characteristics. Different frequencies correspond to different types of shielding.

For a multiply composite material structure, it may be desirable to know the conductivity of the structure in the directions of the ply, transverse to the ply and between plies. Interply conductivity may be particularly important because it can drive lightning performance in terms of edge glow and fastener sparking. For induction heating, knowledge of the interply conductivity may indicate local hot spots.

Techniques currently exist for measuring the interply conductivity of a composite material structure. In one technique, interply conductivity may be measured with current pulse measurements on multiple samples of a specimen structure. This technique requires a direct electrical contact with the specimen and can be time consuming to prepare the samples. In addition, the test itself requires a significant amount of time. Different specimen structures often yield different interply conductivities, but it is not known if this is due to variations in the test specimen, or in the test itself. The current technique requires machining, sanding and plating the specimen structures into small, close-tolerance specimens; and after the structures are tested, they cannot be used again. It is a long and laborious process to characterize the interply conductivity for a new composite material structure. Measured values need to be corrected for contact resistance.

There is also no reliable method to monitor corrosion degradation for some types of specimens when subjected to environmental conditioning. Existing techniques require touching them with a probe, typically after sanding through the resin layer on composites. This can lead to more degradation than if the specimen was left fully intact throughout the entire conditioning. This is especially problematic for salt spray which requires checking specimens at regular intervals as the sanding creates a water path that can accelerate corrosion. Co-curing or installing special features for the probe to touch instead of sanding changes the test article.

Therefore, it may be desirable to have a system and method that takes into account at least some of the issues discussed above, as well as possibly other issues.

BRIEF SUMMARY

Example implementations of the present disclosure are generally directed to an improved system and method for non-destructive testing (NDT) of a composite material structure with at least one electrically conductive layer or feature that forms a structure whose electrical conductivity may be anisotropic. A carbon fiber reinforced plastic (CFRP) panel is one example of a suitable structure, although there are others. The system and method avoid destroying or otherwise modifying the structure. And in addition, the system and method may allow for in-service assessments for maintenance and repair of parts or other structures where there may be adequate access.

The system may include a pair of coils in which a structure under test (SUT) (e.g., CFRP panel) may be placed between. One of the coils may be driven with a source over a broad frequency range, and measurements of the voltage on the other coil may be taken. The shielding effectiveness of the SUT may be measure the shielding effectiveness, and consequently calculate its electrical conductivity. In some examples, such as in the case of a multiply SUT, measurements may be taken with sets of coils of different sizes. Because the conductivity in the interply direction scales differently than in the ply direction, the responses from different coil sizes may be used to determine the interply conductivity.

According to one aspect of example implementations, a method is provided that includes setting up a composite material structure under test (SUT) between a transmit coil and a receive coil. The method includes driving the transmit coil with a radio frequency (RF) signal over a plurality of frequencies, thereby causing the transmit coil to produce a magnetic field that by magnetic coupling through the SUT induces a voltage in the receive coil. The method includes measuring the voltage in the receive coil, and from the voltage, producing a measurement of attenuation of the RF signal over the plurality of frequencies caused by the SUT between the transmit coil and receive coil. And the method includes calculating an effective conductivity of the SUT from the measurement of attenuation.

In some examples, the effective conductivity has components in respective orthogonal axes of a global coordinate system. In these examples, calculating the effective conductivity includes calculating specifically one or more of the components, such as in a manner including performing a finite element analysis according to a finite element model of an arrangement including the transmit coil and receive coil, and the SUT therebetween.

In some examples, the SUT has opposing major surfaces parallel to the transmit coil and receive coil, and the components of the effective conductivity include a first component parallel to the major surfaces of the SUT. In these examples, calculating specifically one or more of the components includes calculating specifically the first component.

In some examples, the SUT has embedded fibers oriented parallel to a principal axis of a local coordinate system. In these examples, calculating specifically one or more of the components includes calculating specifically one or more of the components further from any angular offset of the principal axis of the local coordinate system from a corresponding one of the respective orthogonal axes of the global coordinate system.

In some further examples, the SUT is a multiply structure including a first ply with embedded fibers orientated parallel to a first principal axis of a first local coordinate system, and a second ply with embedded fibers orientated parallel to a second principal axis of a second local coordinate system. In these even further examples, calculating specifically one or more of the components includes calculating specifically one or more of the components further from any angular offset of each of the first principal axis of the first local coordinate system and second principal axis of the second local coordinate system from the corresponding one of the respective orthogonal axes of the global coordinate system.

In some examples, the transmit coil and receive coil form an arrangement. In these examples, the setting up, driving and measuring are performed for a first arrangement in which the transmit coil and receive coil have a first diameter to produce a first measurement of attenuation. The setting up, driving and measuring are repeated for a second arrangement in which the transmit coil and receive coil have a different, second diameter to produce a second measurement of attenuation. Calculating specifically one or more of the components, then, includes calculating specifically one or more of the components from the first measurement of attenuation and second measurement of attenuation. Here, a finite element analysis for calculating specifically one or more of the components may be performed according to finite element models of the first arrangement and second arrangement, each with the SUT therebetween.

In other aspects of example implementations, a system is provided for non-destructive testing of a SUT. The features, functions and advantages discussed herein may be achieved independently in various example implementations or may be combined in yet other example implementations further details of which may be seen with reference to the following description and drawings.

BRIEF DESCRIPTION OF THE DRAWING(S)

Having thus described example implementations of the disclosure in general terms, reference will now be made to the accompanying drawings, which are not necessarily drawn to scale, and wherein:

DETAILED DESCRIPTION

Figure 1:
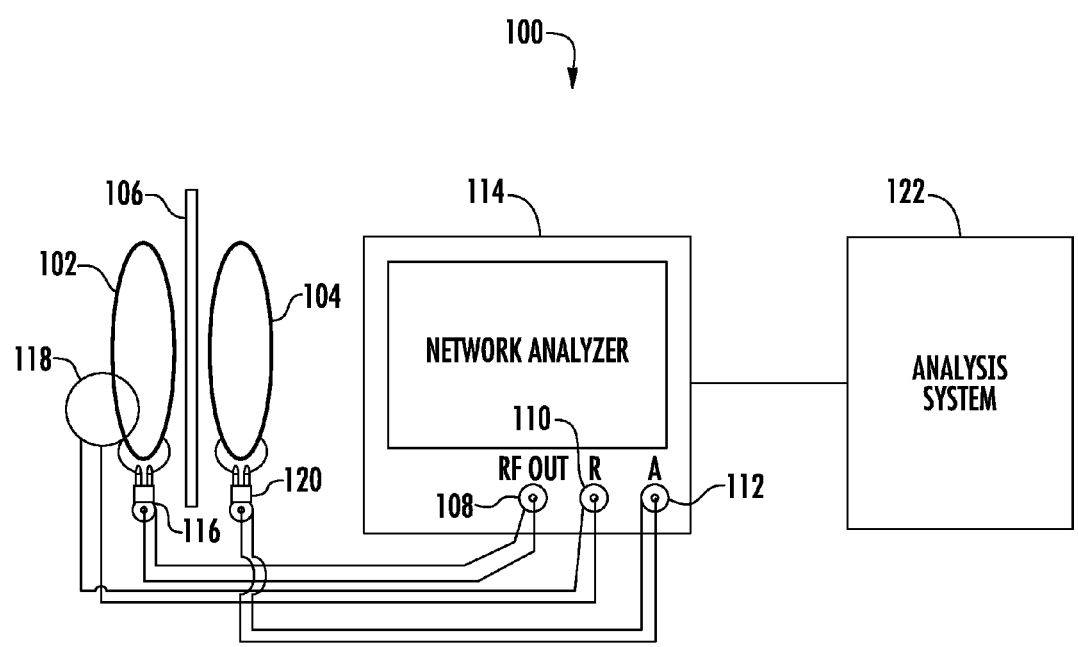
FIG. 1 is an illustration of a system according to example implementations of the present disclosure.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. For example, unless otherwise indicated, reference something as being a first, second or the like should not be construed to imply a particular order. Also, something may be described as being above something else (unless otherwise indicated) may instead be below, and vice versa; and similarly, something described as being to the left of something else may instead be to the right, and vice versa. Like reference numerals refer to like elements throughout.

FIG. 1 illustrates a system 100 according to various example implementations of the present disclosure. The system may be for non-destructive testing of a conductive composite material structure with anisotropic conductivity. The structure may have a controlled geometry, such as in the case of a carbon fiber reinforced plastic (CFRP) panel. Other examples of suitable structure include metalized layers that may be co-cured or attached to dielectric substrates or conductive substrates. These metalized layers such as nickel-coated fibers, interwoven wire, expanded foils, conductive appliqué, and the like. These and similar structures may be characterized for both their acreage properties as well as the conductivity of their splices.

As shown, the system may include an arrangement including a transmit electromagnetic coil 102 and a receive electromagnetic coil 104 (an electromagnetic coil at times simply referred to as a coil). In some examples, the transmit and receive coils may be 50-turn coils, and may be spaced apart a distance less than or equal to the radius of the coils. For example, transmit and receive coils having a radius of approximately 2.5 inches (diameter of approximately 5 inches) may be spaced apart a distance less than or equal to approximately 2.5 inches.

The transmit and receive coils 102, 104 may be configured to receive a structure under test (SUT) 106 between them, with the SUT in some examples being a specific instance of the conductive composite material structure undergoing non-destructive testing. In some examples, the SUT may be received between the coils such that the SUT does not physically contact either of the coils. In the case of a CFRP panel, the SUT of some examples may have a thickness between approximately 1/16 inch and 1 inch.

The transmit and receive coils 102, 104 may be coupled to a signal generator 108, and a pair of receivers 110, 112 and signal processing circuitry, which in some examples may be provided by a network analyzer 114. In some examples, the transmit coil may be coupled to the signal generator by an appropriate banana-to-BNC adapter 116, and one of the pair of receivers by an appropriate current probe 118. Similarly, in some examples, the receive coil may be coupled to the other of the pair of receivers by an appropriate banana-to-BNC adapter 120. Example implementations of the present disclosure may be described below in the context of the network analyzer including the signal generator, and a pair of receivers and signal processing circuitry. It should be understood, however, that any one or more of the respective components may be standalone components, and that a network analyzer may not be required.

The signal generator 108 coupled to the transmit coil 102 may be configured to generate a radio frequency (RF) signal over a plurality of frequencies in a desired frequency range, such as 100 Hz to 10 MHz. The signal generator may thereby drive the transmit coil with the RF signal over the plurality of frequencies. The RF signal may be in the form of a current through the transmit coil (measured at one of the receivers shown as channel R), and cause the transmit coil to produce a magnetic field that by magnetic coupling through the SUT 106 induces a voltage in the receive coil 104 (measured at the other of the receivers shown as channel A). The pair of receivers 110, 112 and signal processing circuitry coupled to the transmit and receive coils may be configured to measure the voltage ($V_A$) in the receive coil divided by the current ($/I_R$) through the transmit coil ($V_A/I_R$).

In some examples, before measuring the SUT 106, the system 100 may be calibrated over the desired frequency range without a structure between the transmit and receive coils 102, 104, and thereby remove frequency dependent responses that may not be related to the SUT, such as the frequency response of the transmit and receive coils 102, 104 or current probe 118. In this regard, the process of operating the system similar to above may be carried out but without a structure between the coils, and a measurement of the voltage ($V_1$) in the receive coil may be produced. A highly-conductive, non-magnetic metal structure such as an aluminum panel may then be received between the coils, and the process repeated to produce a measurement of the voltage ($V_{panel}$) in the receive coil, which can then be referenced to the calibration measurement ($V_{panel}/V_1$).

In some examples, the highly-conductive, non-magnetic structure may be electrically thick (e.g., more than three skin depths thick), and significantly attenuate the fields that diffuse through the structure. The highly-conductive, non-magnetic structure may be electrically thicker than the SUT 106 so that the measured attenuation of the SUT may be bounded by the measured attenuation of the highly-conductive, non-magnetic structure (high attenuation bound), and the measured attenuation without any structure (low attenuation bound). The measured attenuation of the highly-conductive, non-magnetic structure may be limited by the fields that wrap around the edges of the structure, and serve as a noise floor for the measurement from the SUT.

Figure 2:
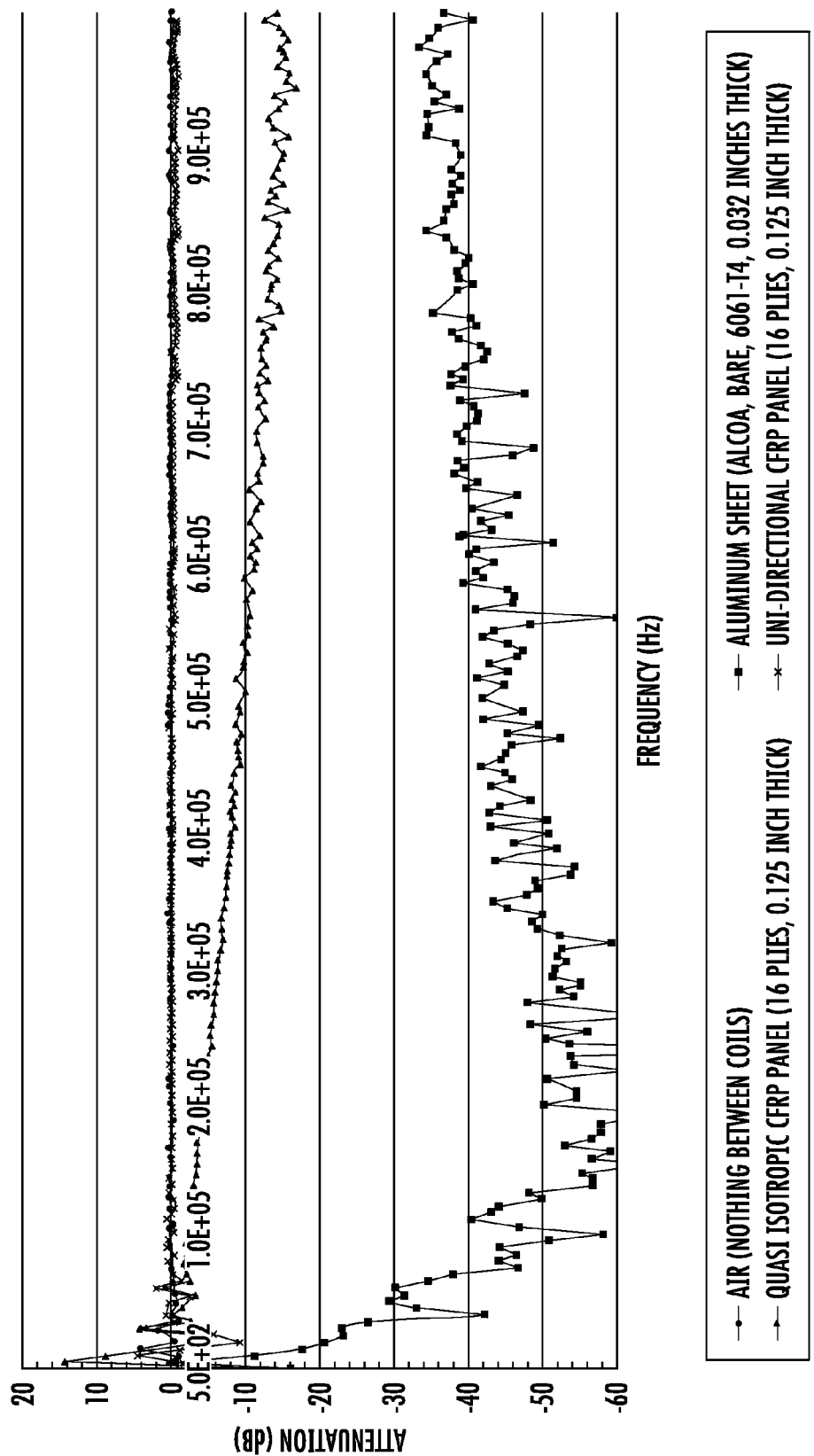
FIG. 2 is a graph illustrating attenuation over the desired frequency range in a number of different contexts, according to example implementations.

The pair of receivers 110, 112 and signal processing circuitry of the network analyzer 114 may produce a measurement of attenuation of the RF signal over the plurality of frequencies caused by the SUT 106 between the transmit and receive coils 102, 104. FIG. 2 is a graph illustrating attenuation over the desired frequency range in a number of different contexts, according to example implementations of the present disclosure. That is, the graph illustrates measurements of attenuation in the context of the system without a structure between the coils, and in contexts of the system with various structures between the coils including a highly-conductive, non-magnetic aluminum panel, a quasi-isotropic CFRP panel and a uni-directional CFRP panel. The measurement of attenuation for the aluminum panel is low and may appear as noise (high attenuation bound), while that in the context of the system without a structure between the coils is approximately 0 dB over the desired frequency range (low attenuation bound).

The measurement of attenuation of the RF signal may reflect attenuation of the magnetic field produced by the transmit coil 102 as a function of frequency. The attenuation may be a function of effective conductivity ($\sigma_{eff}$), frequency ($\omega$), magnetic permeability ($\mu$) and thickness (t) of the SUT, or notationally:

$$\text{Attenuation} = f(\sigma_{eff}, \omega, \mu, t)$$

In some examples, the SUT 106 may be non-magnetic and have a relative permeability of approximately one ($\mu_r \approx 1$). The frequency ($\omega$) and thickness (t) of the SUT may be known, and so a value for the effective conductivity ($\sigma_{eff}$) of the SUT may be calculated from the measurement of attenuation.

To calculate the effective conductivity in some examples, the signal processing circuitry or perhaps more generally the network analyzer 114 may be coupled to an analysis system 122. The attenuation may be a function of the effective conductivity. And the analysis system may be configured to calculate effective conductivity of the SUT from the measurement of attenuation, such as in a manner including the analysis system being configured to perform a finite element analysis according to a finite element model of the arrangement of transmit and receive coils 102, 104 and SUT 106 therebetween.

Figure 3:
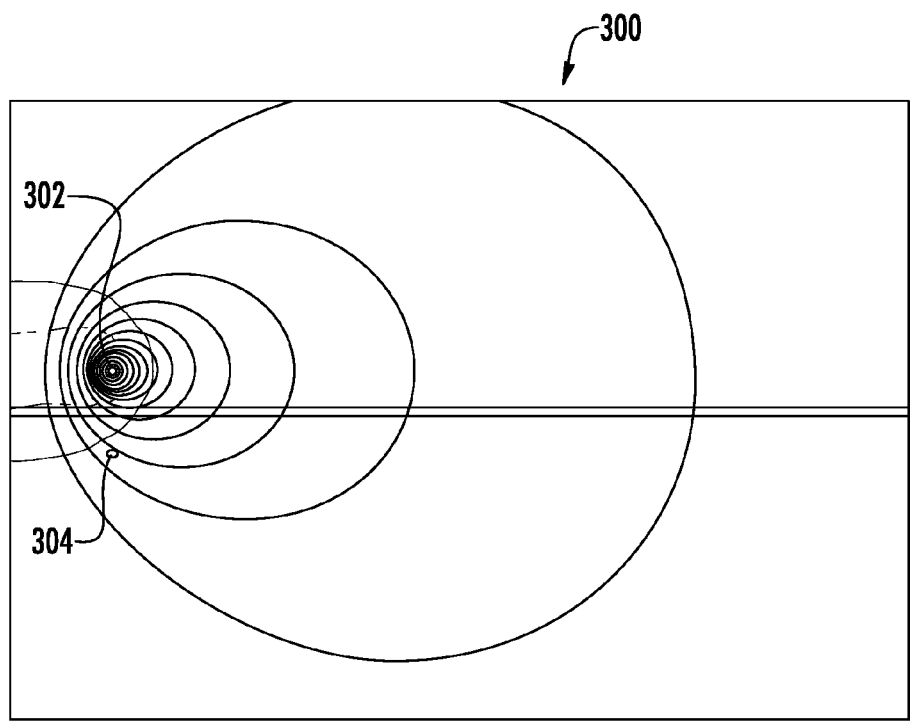
FIGS. 3 and 4 illustrate a two-dimensional, axially-symmetric finite element model in two contexts, in accordance with example implementations.
Figure 4:
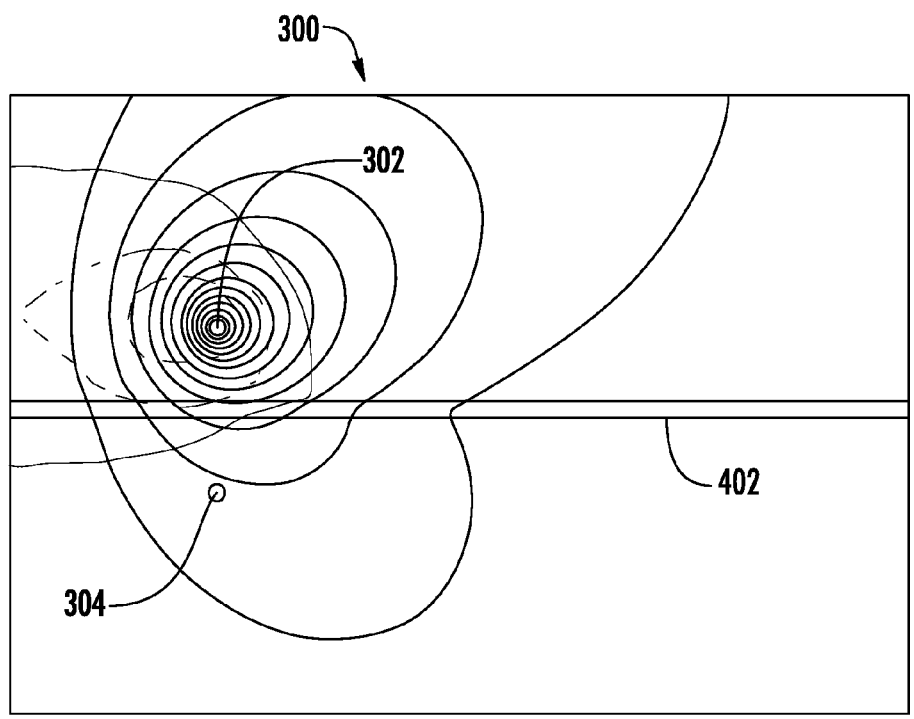

FIGS. 3 and 4 illustrate a two-dimensional, axially-symmetric finite element model 300 in two contexts, in accordance with example implementations of the present disclosure. The model depicts the transmit and receive coils 302, 304. FIG. 3 illustrates the transmit coil driven by a RF signal at one frequency, and shows the magnetic field flux lines from the transmit coil without a structure between the transmit and receive coils. FIG. 4 illustrates the same model with a SUT 402 between the coils, with obvious perturbation to the magnetic field lines. The voltage induced in the receive coil may represent the magnetic field flux linkage, which may be seen as reduced by the SUT.

In some examples, the effective conductivity of the SUT 106 has components in respective orthogonal axes of a global coordinate system (x, y, z), and the analysis system 122 may be configured to calculate specifically one or more of the components. The SUT may have opposing major surfaces parallel to the transmit and receive coils 102, 104, and the components of the effective conductivity may include a first component parallel to the major surfaces of the SUT. The specifically-calculated component(s) may then include at least this first component, which in the context of a multiply SUT may be the interply component of the effective conductivity.

Figure 5:
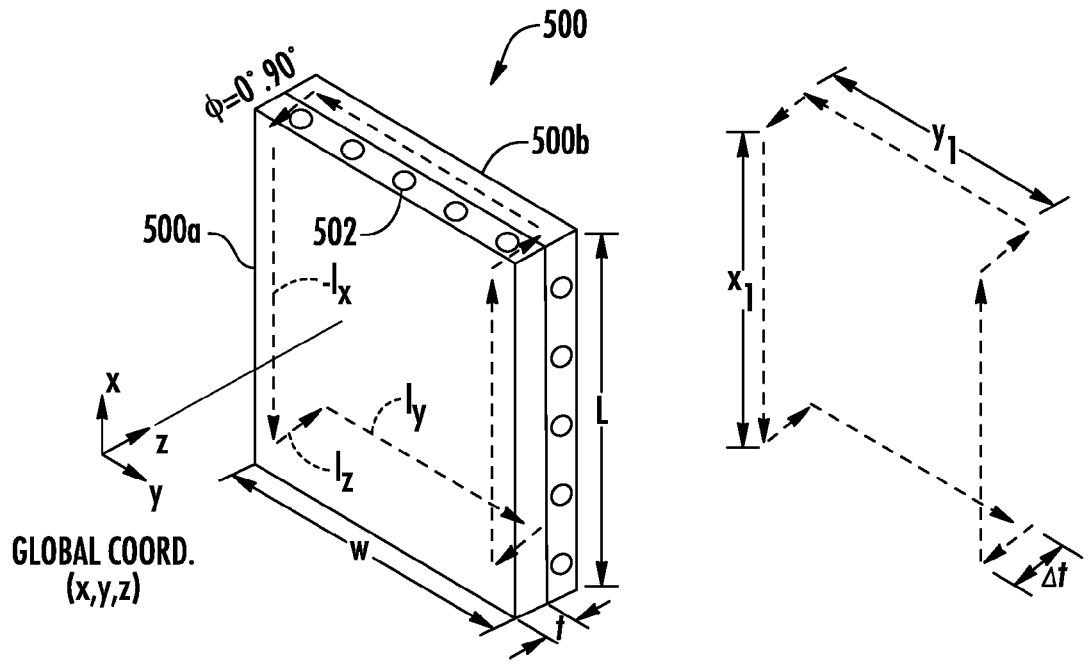
FIG. 5 illustrates an example of a multiply structure that may correspond to a structure under test (SUT), according to some example implementations.
Figure 6:
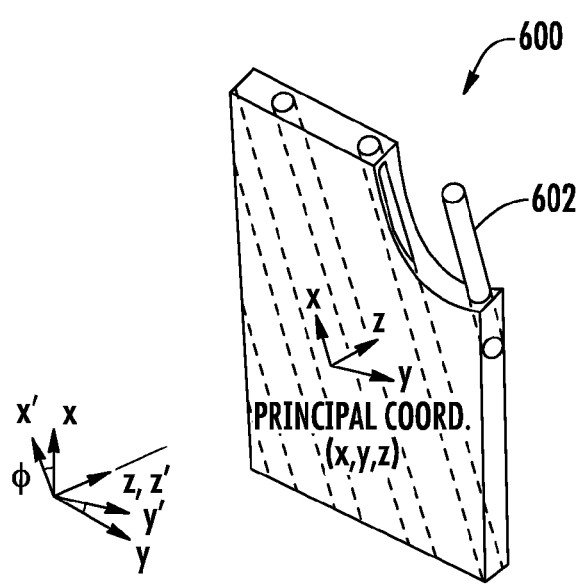
FIG. 6 illustrates a structure that may correspond to a SUT or ply of a multiply SUT, according to some example implementations.

FIG. 5 illustrates an example of a multiply structure 500 including first and second plies 500a, 500b. The structure of FIG. 5 may in some examples correspond to the SUT 106 of FIG. 1, and is illustrated reference to the global coordinate system that in some examples may relate to an electric field that accompanies the magnetic field produced by the transmit coil 102 and incident on the SUT. FIG. 6 illustrates an example of a structure 600 that may correspond to a SUT or ply of a multiply SUT such as the SUT 106 (or ply thereof) of FIG. 1, and with reference to a local coordinate system (shown as principal coordinates) of the SUT/ply.

As also shown in FIGS. 5 and 6, the structure 500, 600 may include embedded fibers 502, 602 oriented parallel to a principal axis (e.g., x'-axis) of the local coordinate system (x', y', z') of the SUT/ply. In some examples, the principal axes of different plies of a multiply SUT may be the same or different, and the local coordinate system of either or both may have an angular offset ($\phi$) from the global coordinate system. In FIG. 5, the fibers and thus the first principal axis of the first ply 500a may be aligned with the global coordinate system ($\phi=0°$), while the fibers and thus the second principal axis of the second ply 500b may be offset from the global coordinate system ($\phi=90°$). In some examples, then, the analysis system 122 may be configured to calculate specifically component(s) of the effective conductivity further from any angular offset of the principal axis (e.g., x'-axis) of the local coordinate system of the SUT/ply from a corresponding one of the respective orthogonal axes (e.g., x-axis) of the global coordinate system.

The effective conductivity of a SUT 106 according to example implementations may be represented as follows:

$$\sigma_{eff} * E = J$$

where E represents the magnitude of an electric field generated in the SUT, and J represents the magnitude of the current density of the in the SUT. The effective conductivity, electric field and current density may also be represented by their components in matrix form as follows:

$$\begin{pmatrix} \sigma_{x,x} & \sigma_{x,y} & \sigma_{x,z} \\ \sigma_{x,y} & \sigma_{y,y} & \sigma_{y,z} \\ \sigma_{x,z} & \sigma_{y,z} & \sigma_{z,z} \end{pmatrix} \cdot \begin{pmatrix} E_x \\ E_y \\ E_z \end{pmatrix} = \begin{pmatrix} J_x \\ J_y \\ J_z \end{pmatrix}$$

Even further, for an inhomogeneous, multiply SUT, each of the plies may have a conductivity matrix as follows:

$$\vec{J} = \begin{pmatrix} J_x \\ J_y \\ J_z \end{pmatrix} = \begin{pmatrix} \sigma_{xx} & 0 & 0 \\ 0 & \sigma_{yy} & 0 \\ 0 & 0 & \sigma_{zz} \end{pmatrix} \cdot \vec{E} = \begin{pmatrix} \sigma_{xx} & 0 & 0 \\ 0 & \sigma_{yy} & 0 \\ 0 & 0 & \sigma_{zz} \end{pmatrix} \begin{pmatrix} E_x \\ E_y \\ E_z \end{pmatrix}$$

In instances in which the global coordinate system aligns with the principal axis of the SUT 106 or ply of a multiply SUT, if it is assumed that the incident electric field does not have a z-axis component, the conductivity matrix may be expressed as:

$$\vec{J} = \begin{pmatrix} J_x \\ J_y \end{pmatrix} = \begin{pmatrix} \sigma_{xx} & 0 \\ 0 & \sigma_{yy} \end{pmatrix} \cdot \vec{E} = \begin{pmatrix} \sigma_{xx} & 0 \\ 0 & \sigma_{yy} \end{pmatrix} \begin{pmatrix} E_x \\ E_y \end{pmatrix}$$

In other instances in which the global coordinate system does not align with the principal axis of the SUT/ply, $$\vec{J} = \begin{pmatrix} J_x \\ J_y \end{pmatrix} = \begin{pmatrix} \sigma_{xx} & \sigma_{xy} \\ \sigma_{xy} & \sigma_{yy} \end{pmatrix} \cdot \vec{E} = \begin{pmatrix} \sigma_{xx} & \sigma_{xy} \\ \sigma_{xy} & \sigma_{yy} \end{pmatrix} \begin{pmatrix} E_x \\ E_y \end{pmatrix}$$

and the conductivity matrix may be rotated by an angle $\phi$ to eliminate the cross terms $\sigma_{xy}$:

$$\vec{J} = \begin{pmatrix} J_x \\ J_y \end{pmatrix}$$

$$= \begin{pmatrix} \cos(\phi) & -\sin(\phi) \\ \sin(\phi) & \cos(\phi) \end{pmatrix} \cdot \begin{pmatrix} \sigma_{xx} & 0 \\ 0 & \sigma_{yy} \end{pmatrix} \cdot \begin{pmatrix} \cos(\phi) & -\sin(\phi) \\ \sin(\phi) & \cos(\phi) \end{pmatrix}^{-1} \cdot \begin{pmatrix} E_x \\ E_y \end{pmatrix}$$

The effective conductivity matrix for a SUT/ply may therefore be expressed as follows:

$$\sigma_{eff} = \begin{bmatrix} \sigma_{yy} \cdot \sin(\phi)^2 + \sigma_{xx} \cdot \cos(\phi)^2 & \sin(\phi) \cdot \cos(\phi) \cdot (\sigma_{xx} - \sigma_{yy}) \\ \sin(\phi) \cdot \cos(\phi) \cdot (\sigma_{xx} - \sigma_{yy}) & \sigma_{xx} \cdot \sin(\phi)^2 + \sigma_{yy} \cdot \cos(\phi)^2 \end{bmatrix}$$

The effective conductivity of a multiply SUT may then be calculated from the above equation for $\sigma_{eff}$ as the sum of the per-ply effective conductivity, each accounting for any angular offset of the principal axis of the ply from the global coordinate system. In one example in which a multiply SUT includes plies oriented with angular offsets of $\phi=0°$, 90° and +/−45°, the effective conductivity of the SUT may be calculated as follows:

$$\sigma_{eff\_SUT} = n_0 \sigma_{eff}(0°) + n_{90} \sigma_{eff}(90°) + n_{45} \sigma_{eff}(45°) + n_{-45} \sigma_{eff}(-45°)$$

where $n_0$, $n_{90}$, $n_{45}$ and $n_{-45}$ represent the number of 0° plies, 90° plies, 45° plies and −45° plies, respectively.

The analysis system 122 may utilize a finite element analysis tool to calculate the $\sigma_{eff}$, which may be particularly beneficial for more complex drives, such as fields from the transmit coil 102 incident on a multiply SUT. One example of a suitable finite element analysis tool is COMSOL Multiphysics® (FEMLAB), available from COMSOL Inc. of Burlington, Mass. In some examples, the components of the effective conductivity of a single ply of a multiply SUT may be entered into the finite element analysis tool, which can then calculate the effective conductivity for the combination of plies of the SUT when driven by a complex field drive. In some examples, the effective conductivity in the direction of the principal axis of the ply (e.g., $\sigma_{xx}$) may be known, which leaves only two unknown components ($\sigma_{yy}$, $\sigma_{zz}$).

Figure 7A:
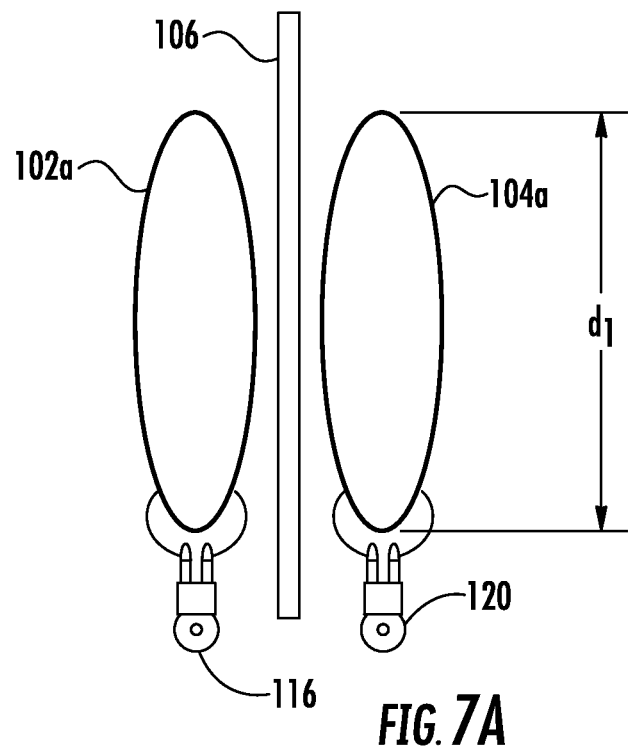
FIGS. 7A and 7B illustrate arrangements of transmit and receive electromagnetic coils of different, respective diameters, according to some example implementations.
Figure 7B:
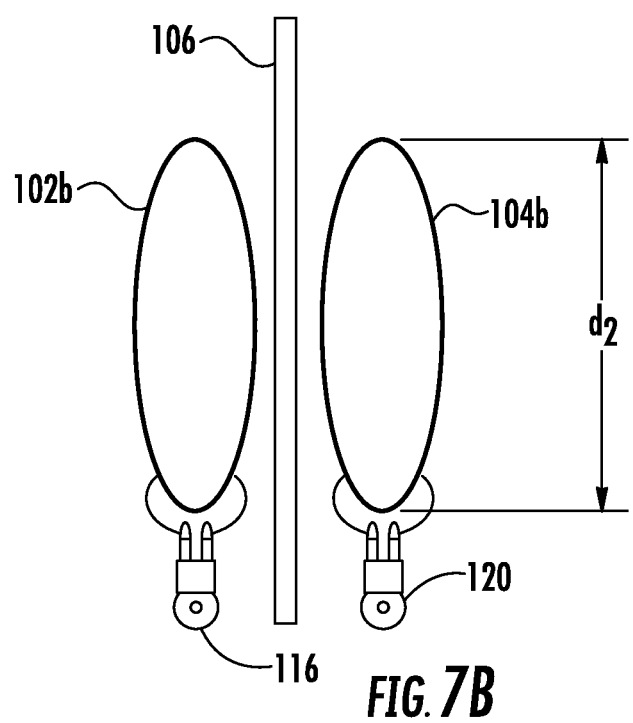

In some examples, it may be desirable to repeat the above for arrangements with different diameter coils to produce multiple, independent expressions from which multiple unknown components of the effective conductivity of the SUT 106 may be calculated. As shown in FIGS. 7A and 7B, the arrangement may include a first arrangement in which the transmit and receive coils 102a, 104a have a first diameter $d_1$, and a second arrangement in which in which the transmit and receive coils 102b, 104b have a different, second diameter $d_2$. In these examples, the signal generator 108 may be configured to separately drive the transmit coil of the first arrangement and second arrangement. Likewise, the pair of receivers 110, 112 and signal processing circuitry may be configured to separately produce a first measurement of attenuation of the RF signal for the first arrangement, and a second measurement of attenuation of the RF signal for the second arrangement. The analysis system 122 may then be configured to calculate specifically component(s) of the effective conductivity from the first measurement of attenuation and second measurement of attenuation. Here, a finite element analysis for calculating specifically component(s)

of the effective conductivity may be performed according to finite element models of the first arrangement and second arrangement.

Further to the above aspect involving multiple sets of coils 102, 104, reference is returned to FIG. 5, which also illustrates the eddy current path in and between first and second plies 500a, 500b that may be induced in the multiply structure 500, and then separately the same current path with dimensions for it. Also, for ease of explanation, a square current path may be assumed, although the current path may be more circular. In SUTs such as this, it can be shown that the effective conductivity ($\sigma_{eff}$) does not scale with the size of the current path. Thus using two sets of coils of different diameters may generate two independent equations for which the two unknowns, $\sigma_{yy}$ and $\sigma_{zz}$ may be calculated.

In the multiply structure 500 of a known length (L), width (w) and thickness (t), current flow in the first ply 500a may spread out the width of the structure, so that the resistance in the x-direction may be as follows:

$$R_x = 1/(\sigma_{xx} * t) * (L/w) = 1/(\sigma_{xx} * \Delta t) * (x_1/y_1)$$

where $x_1$, $y_1$ and $\Delta t$ represent the dimensions of the current path in the x-, y- and z-directions, respectively.

On reaching its furthermost point in the x-direction in the first ply 500a, the current may attempt to flow in the y-direction in the first ply, but the y-directed conductivity may be sufficiently large that the current instead flows from the first ply to the second ply 500b in the z-direction. Although the z-directed conductivity is often the lowest, the distance (t) the current must transition is often very small. This may leads to the current transitioning between plies and flowing along the principle axis of the second ply, as opposed to remaining in the first ply and flowing in the y-direction perpendicular to the principle axis.

The resistance in the z-direction may be expressed as:

$$R_z = \Delta t/(\sigma_{zz} * x_1 * y_1)$$

The resistance in the second ply 500b (a 90° ply) may be expressed in a manner similar to the resistance in the first ply 500a, such as follows:

$$R_y = 1/(\sigma_{xx} * \Delta t) * (y_1/x_1)$$

where $\sigma_{xx}$ here is the effective conductivity in the principle axis of the second ply. And the total resistance for the loop may then be expressed as:

$$R_{Total} = 2*R_x + 2*R_y + 4*R_z$$

For a square current path for a square structure 500 in which L=w and $x_1=y_1$, $R_x$ and $R_y$ may scale as $(x_1/x_1)$, so increasing the size of the current loop may not appreciably change $R_x$ and $R_y$. However, $R_z$ scales as $(1/w*L)$, so increasing the loop size may have a significant impact on $R_z$. For two different sets of transmit and receive coils 102, 104 of different diameters, then, $R_{Total}$ does not scale proportionally with the size of the current path. Different coil sizes may therefore yield two different values for $R_{Total}$ from which the conductivity value in the y- and z-directions ($\sigma_{yy}$, $\sigma_{zz}$) may be calculated.

Fields from the transmit and receive coils 102, 104 and their interaction with the SUT 106 may be complicated, which may create difficulties in analytically solving the problem. As suggested above, then, the analysis system 122 may solve the electromagnetic eddy current flow in the SUT using a finite element analysis tool such as COMSOL that can handle the geometric complexities. The conductivity matrix has three unknowns for its orthogonal-axis components ($\sigma_{xx}$, $\sigma_{yy}$, $\sigma_{zz}$), but one of these components (e.g., $\sigma_{xx}$) may actually be known—thereby reducing the complexity of the problem to two unknowns ($\sigma_{yy}$, $\sigma_{zz}$). Values for these unknowns may be assumed until the measured $\sigma_{eff}$ can be matched.

In some examples, the geometry of the SUT 106, such as its thickness or the thickness of its plies in the case of a multiply SUT, the number and directions of the plies, and the like, may be well known and well controlled. An appropriate finite element model may be run over a plurality of frequencies in the desired frequency range, with fixed transmit and receive coils 102, 104 driven with a known RF signal current. The network analyzer 114 may calculate the magnetic flux linkage to the receive coil (accounting for the attenuation for the unknown panel), which may be used to calculate the receive coil voltage. The analysis system 122 may model the arrangement for multiple sets of coils of different diameters, and calculate or otherwise adjust values for $\sigma_{yy}$ and $\sigma_{zz}$ to match the results from measurements.

Figure 8:
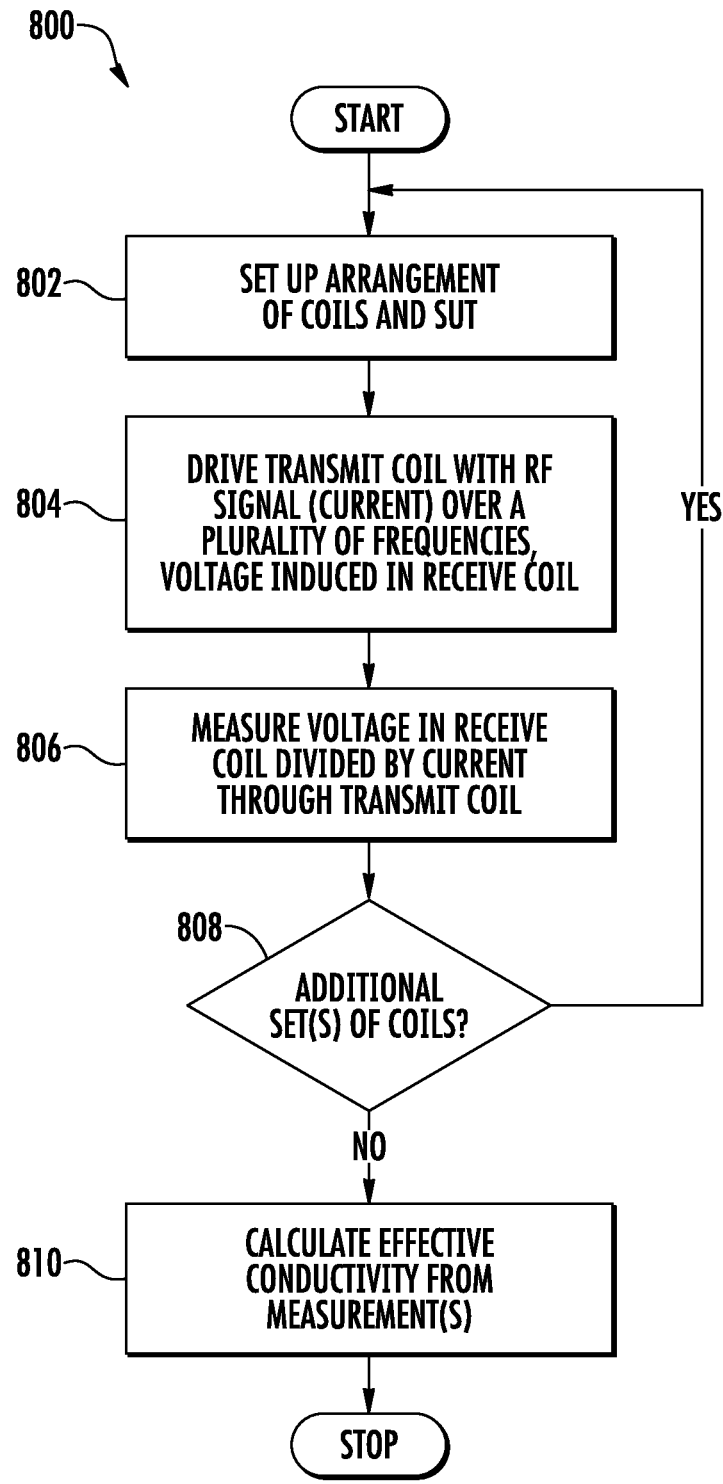
FIG. 8 is a flowchart illustrating various steps in a method according to some example implementations.

FIG. 8 is a flowchart illustrating various steps in a method 800 according to some example implementations of the present disclosure. As shown at block 802, the method may include setting up an arrangement including a SUT 106 between transmit and receive coils 102, 104, with the SUT being a conductive composite material structure with anisotropic conductivity. The method may include driving the transmit coil with a RF signal over a plurality of frequencies, as shown in block 804. The RF signal may be in the form of a current through the transmit coil, which may cause the transmit coil to produce a magnetic field that by magnetic coupling through the SUT induces a voltage in the receive coil. The method may include measuring the voltage in the receive coil divided by the current through the transmit coil, as shown in block 806. This produces a measurement of attenuation of the RF signal over the plurality of frequencies caused by the SUT between the transmit and receive coils. In some examples, these steps may be repeated for first and second arrangements in which the transmit and receive coils have first and different, second diameters to produce respectively first and second measurements of attenuation, as shown in block 808. And the method may include calculating effective conductivity of the SUT from the measurement of attenuation (or first and second measurements of attenuation), with the attenuation being a function of the effective conductivity, as shown in block 810.

In accordance with example implementations, the effective conductivity of a SUT 106 may be calculated as an absolute value or a relative change in effective conductivity for the SUT, and may be useful in a number of contexts. For example, the effective conductivity of a SUT may be calculated at regular intervals while it is being environmentally conditioned. Particularly when just screening material structures, it may be more cost effective to simply plot the measurements with one set of transmit and receive coils 102, 104 to monitor the relative difference over time. At the conclusion of the environmental conditioning, instances of the material structure may be weighed, destructively inspected and measured using traditional conductivity measurements to better understand the value of example implementations. These changes in the effective conductivity may then be correlated to corrosion, cracking or other degradation mechanisms, and used for future tests.

In other examples in which a material structure is being qualified for a specific application, a more sophisticated algorithm approach and measurements from multiple sets of transmit and receive coils 102, 104 may be beneficial to optimize shielding and/or lightning design.

Consider painted metalized composites, which is a particular type of material structure with no known reliable way to monitor conductivity during moisture conditioning without compromising its integrity. In other cases, examples of types of material structures for lightning protection whose conductivity is often challenging to characterize include woven metal fabrics, expanded foils and interwoven wire fabric (metal wires combined with carbon fabric). These can be bonded or co-cured with composites. They have some form of resin on the exterior of the air or space vehicle that provides a smooth surface for painting and some environmental protection. Traditional resistance measurement techniques require sanding through the protective resin layer to reach the metal to get a reliable measurement. This sanding of the resin layer, as well as removing the paint on top of the resin, compromises the test. Leaving tape or paint off the edges to give the probe access also compromises the specimen. Many different techniques have been tried with existing resistant measurement techniques but none are both reliable and cost-effective.

Often an "X" is scribed in instances of the material structure to make a preferred corrosion location, which may further complicate the use of traditional conductivity measurements.

Example implementations of the present disclosure may be used prior to starting the conditioning of instances of a material structure and then periodically during and following an extended duration (e.g., 3000 hour) humidity exposure. Example implementations may only take a couple of minutes to run, and may not compromise the paint or resin. Edges of the structure may be painted and/or taped because no probes are required. Example implementations may be used to characterize both structures with no splices to characterize acreage, and spliced structures where the type and sizes of metallic splices are varied. Splices tend to corrode more than acreage so it may be important to size them properly based on expected degradation. Example implementations may also benefit metalized hybrids. In instances in which at least one layer is conductive, there may be value in at least relative measurements.

It is well established the conductivity impacts electromagnetic effects (EME) such as lightning, shielding, and precipitation static and electrostatic performance. Even knowing relative performance of a material structure may provide significant benefit. The relationship between cracking and EME performance is less well established. Example implementations may provide a low cost nonintrusive method to assess other variables. Example implementations may be used in conjunction with hydrothermal cycling to assess micro-cracking and corrosion. Sanding to provide probe access to the embedded metallic lightning protection for a traditional resistance measurement may also impact those results. Similar to humidity tests, destructive inspection at the need of the test may be used in conjunction with data from example implementations to assess a material's performance.

Another example where one-sized coils relative comparison may be establishing initial test levels for lightning spark tests, particularly when there is already data on the same material but with a different configuration or a similar material. This can reduce the number of specimens and the time to do the test.

According to example implementations of the present disclosure, the analysis system 122 may be implemented by various means, which may include hardware, alone or under direction of one or more computer program code instructions, program instructions or executable computer-readable program code instructions from a computer-readable storage medium. In one example, one or more apparatuses may be provided that are configured to function as or otherwise implement the analysis system. In examples involving more than one apparatus, the respective apparatuses may be connected to or otherwise in communication with one another in a number of different manners, such as directly or indirectly via a wireline or wireless network or the like.

Figure 9:
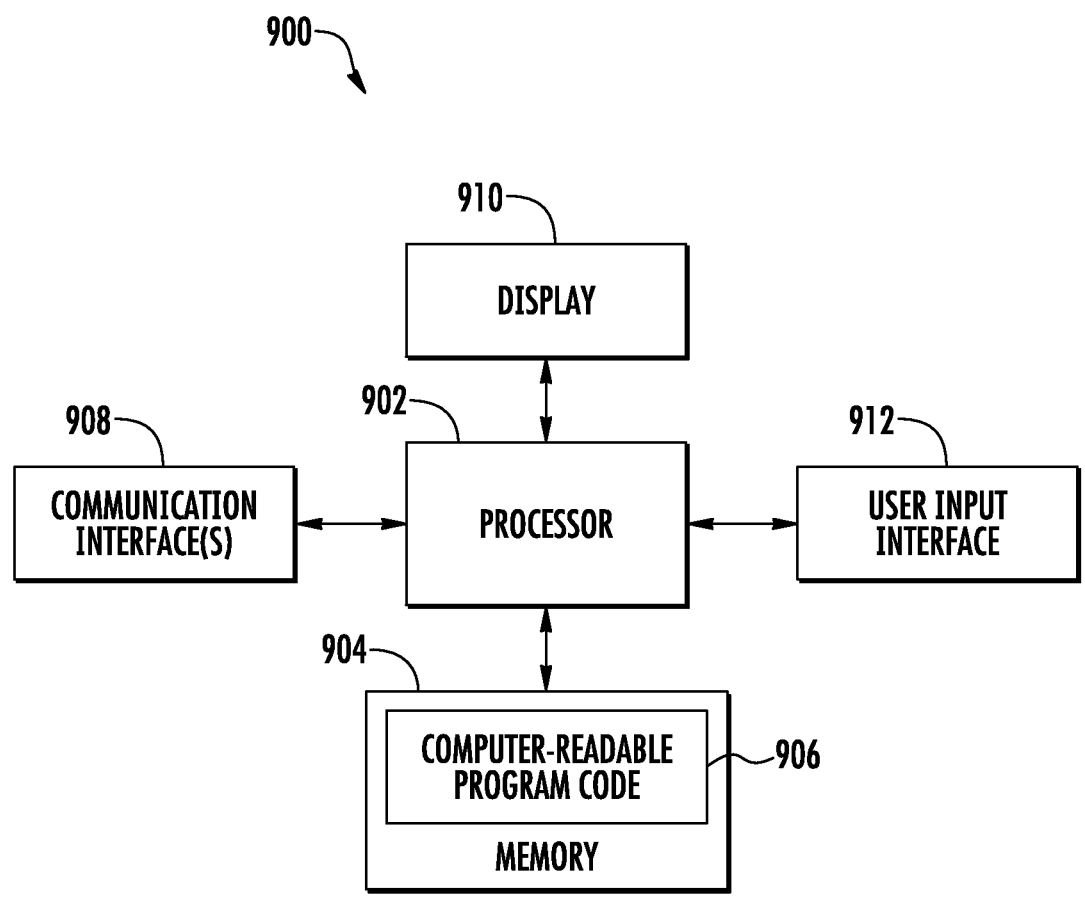
FIG. 9 illustrates an apparatus that according to some examples may be configured to at least partially implement an analysis system of the system of FIG. 1.

FIG. 9 illustrates an apparatus 900 that according to some examples may be configured to at least partially implement the analysis system 122. Generally, the apparatus of exemplary implementations of the present disclosure may comprise, include or be embodied in one or more fixed or portable electronic devices. Examples of suitable electronic devices include a smartphone, tablet computer, laptop computer, desktop computer, workstation computer, server computer or the like. The apparatus may include one or more of each of a number of components such as, for example, a processor 902 connected to a memory 904.

The processor 902 is generally any piece of computer hardware that is capable of processing information such as, for example, data, computer-readable program code, instructions or the like (at times generally referred to as "computer programs," e.g., software, firmware, etc.), and/or other suitable electronic information. The processor is composed of a collection of electronic circuits some of which may be packaged as an integrated circuit or multiple interconnected integrated circuits (an integrated circuit at times more commonly referred to as a "chip"). The processor may be configured to execute computer programs, which may be stored onboard the processor or otherwise stored in the memory 904 (of the same or another apparatus).

The processor 902 may be a number of processors, a multi-processor core or some other type of processor, depending on the particular implementation. Further, the processor may be implemented using a number of heterogeneous processor systems in which a main processor is present with one or more secondary processors on a single chip. As another illustrative example, the processor may be a symmetric multi-processor system containing multiple processors of the same type. In yet another example, the processor may be embodied as or otherwise include one or more application-specific integrated circuits (ASICs), field-programmable gate arrays (FPGAs) or the like. Thus, although the processor may be capable of executing a computer program to perform one or more functions, the processor of various examples may be capable of performing one or more functions without the aid of a computer program.

The memory 904 is generally any piece of computer hardware that is capable of storing information such as, for example, data, computer programs (e.g., computer-readable program code 906) and/or other suitable information either on a temporary basis and/or a permanent basis. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD or the like. In various instances, the memory may be referred to as a computer-readable storage medium which, as a non-transitory device capable of storing information, may be distinguishable from computer-readable transmission media such as electronic transitory signals capable of carrying information from one location to another. Computer-readable medium as described herein may generally refer to a computer-readable storage medium or computer-readable transmission medium.

In addition to the memory 904, the processor 902 may also be connected to one or more interfaces for displaying, transmitting and/or receiving information. The interfaces may include a communications interface 908 and/or one or more user interfaces. The communications interface may be configured to transmit and/or receive information, such as to and/or from other apparatus(es), network(s) or the like. The communications interface may be configured to transmit and/or receive information by physical (wireline) and/or wireless communications links. Examples of suitable communication interfaces include a network interface controller (NIC), wireless NIC (WNIC) or the like.

The user interfaces may include a display 910 and/or one or more user input interfaces 912. The display may be configured to present or otherwise display information to a user, suitable examples of which include a liquid crystal display (LCD), light-emitting diode display (LED), plasma display panel (PDP) or the like. The user input interfaces may be wireline or wireless, and may be configured to receive information from a user into the apparatus, such as for processing, storage and/or display. Suitable examples of user input interfaces include a microphone, image or video capture device, keyboard or keypad, mouse, joystick, touch-sensitive surface (e.g., touchpad, touchscreen), biometric sensor or the like. The user interfaces may further include one or more interfaces for communicating with peripherals such as printers, scanners or the like.

As indicated above, program code instructions may be stored in memory, and executed by a processor, to implement functions of the systems, subsystems and their respective elements described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, a processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the computer, processor or other programmable apparatus provide operations for implementing functions described herein.

Execution of instructions by a processor, or storage of instructions in a computer-readable storage medium, supports combinations of operations for performing the specified functions. In this manner, an apparatus 900 may include a processor 902 and a computer-readable storage medium or memory 904 coupled to the processor, where the processor is configured to execute computer-readable program code 906 stored in the memory. It will also be understood that one or more functions, and combinations of functions, may be implemented by special purpose hardware-based computer systems and/or processors which perform the specified functions, or combinations of special purpose hardware and program code instructions.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A system comprising:
a transmit coil and a receive coil configured to receive a composite material structure under test (SUT) therebetween;
a signal generator configured to drive the transmit coil with a radio frequency (RF) signal over a plurality of frequencies, the RF signal being in the form of a current through the transmit coil that causes the transmit coil to produce a magnetic field that by magnetic coupling through the SUT induces a voltage in the receive coil;
a pair of receivers and signal processing circuitry coupled to the transmit coil and receive coil, and configured to measure the voltage in the receive coil divided by the current through the transmit coil and thereby produce a measurement of attenuation of the RF signal over the plurality of frequencies caused by the SUT between the transmit coil and receive coil; and
an analysis system coupled to the signal processing circuitry and configured to calculate a conductivity of the SUT from the measurement of attenuation, wherein the conductivity has components in respective orthogonal axes of a global coordinate system, and the analysis system being configured to calculate the conductivity includes being configured to calculate specifically one or more of the components,
wherein the transmit coil and receive coil form an arrangement and include a first arrangement in which the transmit coil and receive coil have a first diameter, and a second arrangement in which the transmit coil and receive coil have a different, second diameter,
wherein the signal generator is configured to separately drive the transmit coil of the first arrangement and second arrangement, and the pair of receivers and signal processing circuitry are configured to separately produce a first measurement of attenuation of the RF signal for the first arrangement, and a second measurement of attenuation of the RF signal for the second arrangement, and wherein the analysis system being configured to calculate specifically one or more of the components includes being configured to calculate specifically one or more of the components from the first measurement of attenuation and second measurement of attenuation.

2. The system of claim 1, wherein the SUT has opposing major surfaces parallel to the transmit coil and receive coil, and the components of the conductivity include a first component parallel to the major surfaces of the SUT, and wherein the analysis system being configured to calculate specifically one or more of the components includes being configured to calculate specifically the first component.

3. The system of claim 1, wherein the analysis system being configured to calculate specifically one or more of the components includes being configured to perform a finite element analysis according to a finite element model of an arrangement including the transmit coil and receive coil, and the SUT received therebetween.

4. The system of claim 1, wherein the SUT has opposing major surfaces parallel to the transmit coil and receive coil, and the components of the conductivity include a first component parallel to the major surfaces of the SUT, and wherein the analysis system being configured to calculate specifically one or more of the components includes being configured to calculate specifically the first component.

5. The system of claim 1, wherein the analysis system being configured to calculate specifically one or more of the components includes being configured to perform a finite element analysis according to finite element models of the first arrangement and second arrangement, each with the SUT received therebetween.

6. The system of claim 1, wherein the SUT has embedded fibers oriented parallel to a principal axis of a local coordinate system, and wherein the analysis system being configured to calculate specifically one or more of the components includes being configured to calculate specifically one or more of the components further from any angular offset of the principal axis of the local coordinate system from a corresponding one of the respective orthogonal axes of the global coordinate system.

7. The system of claim 1, wherein the SUT has embedded fibers oriented parallel to a principal axis of a local coordinate system, and wherein the analysis system being configured to calculate specifically one or more of the components includes being configured to calculate specifically one or more of the components further from any angular offset of the principal axis of the local coordinate system from a corresponding one of the respective orthogonal axes of the global coordinate system.

8. The system of claim 7, wherein the SUT is a multiply structure including a first ply with embedded fibers orientated parallel to a first principal axis of a first local coordinate system, and a second ply with embedded fibers orientated parallel to a second principal axis of a second local coordinate system, and wherein the analysis system being configured to calculate specifically one or more of the components includes being configured to calculate specifically one or more of the components further from any angular offset of each of the first principal axis of the first local coordinate system and second principal axis of the second local coordinate system from the corresponding one of the respective orthogonal axes of the global coordinate system.

9. A method comprising:

setting up a composite material structure under test (SUT) between a transmit coil and a receive coil;

driving the transmit coil with a radio frequency (RF) signal over a plurality of frequencies, the RF signal being in the form of a current through the transmit coil that causes the transmit coil to produce a magnetic field that by magnetic coupling through the SUT induces a voltage in the receive coil;

measuring the voltage in the receive coil divided by the current through the transmit coil and thereby producing a measurement of attenuation of the RF signal over the plurality of frequencies caused by the SUT between the transmit coil and receive coil; and calculating a conductivity of the SUT from the measurement of attenuation, wherein the conductivity has components in respective orthogonal axes of a global coordinate system, and calculating the conductivity includes calculating specifically one or more of the components, wherein the transmit coil and receive coil form an arrangement, wherein the setting up, driving and measuring are performed for a first arrangement in which the transmit coil and receive coil have a first diameter to produce a first measurement of attenuation, and are repeated for a second arrangement in which the transmit coil and receive coil have a different, second diameter to produce a second measurement of attenuation, and wherein calculating specifically one or more of the components includes calculating specifically one or more of the components from the first measurement of attenuation and second measurement of attenuation.

10. The method of claim 9, wherein the SUT has opposing major surfaces parallel to the transmit coil and receive coil, and the components of the conductivity include a first component parallel to the major surfaces of the SUT, and wherein calculating specifically one or more of the components includes calculating specifically the first component.

11. The method of claim 9, wherein calculating specifically one or more of the components includes performing a finite element analysis according to a finite element model of an arrangement including the transmit coil and receive coil, and the SUT therebetween.

12. The method of claim 9, wherein the SUT has opposing major surfaces parallel to the transmit coil and receive coil, and the components of the conductivity include a first component parallel to the major surfaces of the SUT, and wherein calculating specifically one or more of the components includes calculating specifically the first component.

13. The method of claim 9, wherein calculating specifically one or more of the components includes performing a finite element analysis according to finite element models of the first arrangement and second arrangement, each with the SUT therebetween.

14. The method of claim 9, wherein the SUT has embedded fibers oriented parallel to a principal axis of a local coordinate system, and wherein calculating specifically one or more of the components includes calculating specifically one or more of the components further from any angular offset of the principal axis of the local coordinate system from a corresponding one of the respective orthogonal axes of the global coordinate system.

15. The method of claim 9, wherein the SUT has embedded fibers oriented parallel to a principal axis of a local coordinate system, and wherein calculating specifically one or more of the components includes calculating specifically one or more of the components further from any angular offset of the principal axis of the local coordinate system from a corresponding one of the respective orthogonal axes of the global coordinate system.

16. The method of claim 15, wherein the SUT is a multiply structure including a first ply with embedded fibers orientated parallel to a first principal axis of a first local coordinate system, and a second ply with embedded fibers orientated parallel to a second principal axis of a second local coordinate system, and wherein calculating specifically one or more of the components includes calculating specifically one or more of the components further from any angular offset of each of the first principal axis of the first local coordinate system and second principal axis of the second local coordinate system from the corresponding one of the respective orthogonal axes of the global coordinate system.

* * * * *